(12) United States Patent
Kramer et al.

(10) Patent No.: US 6,813,024 B2
(45) Date of Patent: Nov. 2, 2004

(54) NON-FOCUSING OPTICS SPECTROPHOTOMETER, AND METHODS OF USE

(75) Inventors: David M. Kramer, Pullman, WA (US); Colette A. Sacksteder, St. Paul, MN (US)

(73) Assignee: Washington State University Research Foundation, Pullman, WA (US)

( * ) Notice: Subject to any disclaimer, the term of this patent is extended or adjusted under 35 U.S.C. 154(b) by 246 days.

(21) Appl. No.: 09/785,041

(22) Filed: Feb. 13, 2001

(65) Prior Publication Data

US 2001/0030742 A1 Oct. 18, 2001

Related U.S. Application Data

(63) Continuation-in-part of application No. PCT/US00/22754, filed on Aug. 18, 2000.
(60) Provisional application No. 60/149,937, filed on Aug. 19, 1999.

(51) Int. Cl.⁷ ............................. G01J 3/44; G01N 21/64
(52) U.S. Cl. ........................ 356/416; 356/417; 356/72; 250/458.1
(58) Field of Search ................................ 356/300, 319, 356/416, 417, 419; 250/458.1, 459.1, 461.1, 461.2

(56) References Cited

U.S. PATENT DOCUMENTS

| 3,473,022 | A |   | 10/1969 | Walz et al. |
| 4,533,252 | A |   | 8/1985 | Cahen et al. |
| 4,650,336 | A |   | 3/1987 | Moll |
| 4,768,390 | A |   | 9/1988 | Baker et al. |
| 5,029,245 | A | * | 7/1991 | Keranen et al. ............ 356/328 |
| 5,426,306 | A |   | 6/1995 | Kolber et al. |
| 5,519,219 | A | * | 5/1996 | Alexay et al. ......... 250/339.07 |
| 5,854,063 | A |   | 12/1998 | Li et al. |
| 5,981,958 | A |   | 11/1999 | Li et al. |
| 6,005,722 | A | * | 12/1999 | Butterworth et al. ....... 359/712 |
| 6,043,893 | A | * | 3/2000 | Treiman et al. ............. 356/402 |
| 6,121,053 | A |   | 9/2000 | Kolber et al. |

FOREIGN PATENT DOCUMENTS

| DE | 248 433 A1 | 8/1987 |
| DE | 300 049 A7 | 5/1992 |

OTHER PUBLICATIONS

Tanaka, K. et al., "Compound parabolic concentrator probe for efficient light collection in spectroscopy of biological tissue," *Applied Optics*, 35(4):758–636 (1996).

(List continued on next page.)

*Primary Examiner*—F. L. Evans
(74) *Attorney, Agent, or Firm*—Christensen O'Connor Johnson Kindness PLLC

(57) ABSTRACT

In one aspect, the present invention provides kinetic spectrophotometers that each comprise: (a) a light source; and (b) a compound parabolic concentrator disposed to receive light from the light source and configured to (1) intensify and diffuse the light received from the light source, and (2) direct the intensified and diffused light onto a sample. In other aspects, the present invention provides methods for measuring a photosynthetic parameter, the methods comprising the steps of: (a) illuminating a plant leaf until steady-state photosynthesis is achieved; (b) subjecting the illuminated plant leaf to a period of darkness; (c) using a kinetic spectrophotometer of the invention to collect spectral data from the plant leaf treated in accordance with steps (a) and (b); and (d) determining a value for a photosynthetic parameter from the spectral data.

17 Claims, 7 Drawing Sheets

OTHER PUBLICATIONS

Kramer D.M. et al., "A diffused–optics flash kinetic spectrophotometer (DOFS) for measurements of absorbance changes in intact plants in the stead–state," *Photosynthesis Research*, 56:103–112 (1998).

Sacksteder, C.A. et al., "H+/E– Ratios for Photosynthetic Electron Transfer in Intact Leaves in the Steady State," *Photosynthesis: Mechanisms and Effects*, 3:1621–1624 (1998).

Genty, B., et al., "The Relationship Between Non–Photochemical Quenching of Chlorophyll Fluorescence and the Rate of Photosystem 2 Photochemistry in Leaves," *Photosynth. Res.* 25:249–257, 1990.

Joliot, P., and A. Joliot, "Electronic Transfer Between the Two Photosystems: I. Flash Excitation Under Oxidizing Condition," *Biochim. Biophys. Acta* 765:210–218, 1984.

Kramer, D.M., and A.R. Crofts, "Activation of the Chloroplast ATPase Measured by the Electrochromic Change in Leaves of Intact Plants," *Biochim. Biophys. Acta*. 976:28–41, 1989.

Kramer, D.M., and A.R. Crofts, "Control and Measurement of Photosynthestic Electron Transport In Vivo," in N.R. Baker (ed.), *Photosynthesis and the Environment*, Kluwer Academic Publishers, Dordrecht, The Netherlands, 1996, pp. 25–66.

Kramer, D.M., et al., "A Portable Multi–Flash Kinetic Fluorimeter for Measurement of Donor and Acceptor Reactions of Photosystem 2 in Leaves of Intact Plants Under Field Conditions," *Photosynth. Res.* 26:181–193, 1990.

Nishio, J.N., and J. Whitmark, "Dissipation of the Proton Electrochemical Potential in Intact and Lysed Chloroplasts," *Plant Physiol.* 95:522–528, 1991.

Sacksteder, C.A., et al., "The Proton to Electron Stoichiometry of Steady–State Photosynthesis in Living Plants: A Proton–Pumping Q Cycle is Continuously Engaged," *PNAS* 97926):14283–14288, 2000.

* cited by examiner

NON-FOCUSING OPTICS SPECTROPHOTOMETER, AND METHODS OF USE

CROSS-REFERENCES TO RELATED APPLICATIONS

This application is a continuation-in-part of PCT/US00/22754, filed Aug. 18, 2000, which claims the benefit of Provisional Application No. 60/149,937, filed Aug. 19, 1999.

GOVERNMENT RIGHTS

This invention was funded in part by the Department of Energy, Grant No. DE FG03 98ER20299. The United States Government has certain rights in the invention.

FIELD OF THE INVENTION

The present invention relates generally to spectrophotometers, to methods for measuring a photosynthetic parameter, and to methods for determining the physiological state of a plant.

BACKGROUND OF THE INVENTION

Photosynthesis in green plants takes place in two stages, the light reactions, which occur only when plants are illuminated, and the dark reactions, which can occur in the absence or presence of light. In the light reactions chlorophyll and other pigments of the photosynthetic cells absorb light energy and conserve it in chemical form as the two energy-rich products adenosine triphosphate (ATP) and nicotinamide adenine dinucleotide phosphate (NADPH); simultaneously, oxygen is evolved. In the dark reactions, the ATP and NADPH generated in the light reactions are used to reduce carbon dioxide to form glucose and other organic products.

In eukaryotic, photosynthetic cells, both the light and dark reactions take place in the chloroplast. Chloroplasts are surrounded by a continuous outer membrane. An inner membrane system encloses the internal compartment. Inside the latter, and often connected to the inner membrane, are many flattened, membrane-surrounded vesicles or sacs, called thylakoids, which are either single, or arranged in stacks called grana. The thylakoid membranes contain all the photosynthetic pigments of the chloroplast and most of the enzymes required for the primary light-dependent reactions. The fluid in the compartment surrounding the thylakoid vesicles, the stroma, contains most of the enzymes required for the dark reactions (i.e. $CO_2$ fixation).

Light energy is absorbed by photosynthetic pigments located within the thylakoid membranes. The primary light-absorbing pigment is chlorophyll. Photosynthetic cells of higher plants always contain two types of chlorophyll. One is always chlorophyll a, and the second in many species is chlorophyll b. In addition to chlorophylls, the thylakoid membranes contain secondary light-absorbing pigments, together called the accessory pigments, which include various carotenoids. The carotenoid pigments absorb light at wavelengths other than those absorbed by the chlorophylls and thus are supplementary light receptors.

The light-absorbing pigments of thylakoid membranes are arranged in functional sets or clusters called photosystems. The clusters can absorb light over the entire visible spectrum but especially well between 400 to 500 and 600 to 700 nanometers (nm). All the pigment molecules in a photosystem can absorb photons, but a special subset of the molecules, housed in complexes of proteins and cofactors, called the 'photochemical reaction centers' in each cluster ultimately convert the light energy into chemical energy. Other pigment molecules, that function to funnel light into the reaction centers, are housed in light-harvesting complexes. They function to absorb light energy, which they transmit at a very high rate to the reaction center.

There are two different kinds of photosystems: photosystem I (PS I), which is maximally excited by light at longer wavelengths, and has a high ratio of chlorophyll a to chlorophyll b; and photosystem II (PS II), which is maximally activated by light below 680 nm, and contains relatively more chlorophyll b and may also contain chlorophyll c. Photosystem I and Photosystem II are functionally linked by a chain of electron carriers, as shown in FIG. 1.

When light quanta are absorbed by photosystem I, energy-rich electrons are expelled from the reaction center and flow down a chain of electron carriers to $NADP^+$ to reduce it to NADPH. This process leaves a deficit of electrons (an electron hole) in photosystem I. This hole is, in turn, filled by an electron expelled by illumination of photosystem II, which arrives via a connecting chain of electron carriers, including a pool of about 6 plastoquinone molecules per reaction center, the cytochrome $b_6f$ complex and plastocyanin. The resulting electron hole in photosystem II is filled by electrons extracted from water. This pattern of electron flow is usually referred to as the "Z-scheme". Additionally, absorbed light can be reemitted in the form of fluorescence.

The thylakoid membrane has an asymmetric molecular organization. The electron-transferring molecules in the connecting chain between photosystem II and photosystem I are oriented in the thylakoid membrane in such a way that electron flow results in the net movement of $H^+$ ions across the membrane, from the outside of the thylakoid membrane to the inner compartment. Thus photoinduced electron flow generates an electrochemical gradient of $H^+$ ions across the thylakoid membrane, so that: 1) the inside of the thylakoid vesicles becomes more acid than the outside, storing energy as a difference in pH (known as $\Delta pH$); and 2) the inside of the thylakoid membrane becomes more positively charged than the outside, storing energy as an electrical field (known as $\Delta \psi$). The sum of energies stored as $\Delta pH$ and $\Delta \psi$ drives the synthesis of ATP from ADP and inorganic phosphase, for later use in plant biochemical processes.

Lumen acidification also initiates processes that down-regulate the entire photosynthetic apparatus. The down-regulatory processes reduce the amount of light transferred from the light harvesting pigments to the photosystem II reaction centers, thus protecting the reaction centers from over-exposure to light.

Another type of light-induced electron flow that can take place in chloroplasts is called cyclic electron flow, to differentiate it from the normally unidirectional or noncyclic electron flow of the "Z-scheme" that proceeds from $H_2O$ to $NADP^+$. As shown in FIG. 2, cyclic electron flow involves only photosystem I. It is called cyclic because the electron boosted to the first electron acceptor in photosystem I (an iron-sulfur cluster) by illumination of photosystem I, instead of passing to $NADP^+$, flows back into the electron hole of photosystem I by a shunt or bypass pathway. As shown in FIG. 2, this shunt involves some of the electron carriers of the chain between photosystems I and II, including the pool of plastoquinone molecules, the cytochrome $b_6f$ complex and plastocyanin. Thus, illumination of photosystem I can cause electrons to cycle continuously out of the reaction center of photosystem I and back into it. During cyclic electron flow there is no net formation of NADPH, nor is there any oxygen evolution. However, cyclic electron flow is accompanied by proton pumping into the lumen (inside) of the thylakoid vesicle. Thus cyclic electron flow can generate ATP, and this process is referred to as cyclic photophosphorylation. Cyclic electron flow is thought to have two functions: to supply ATP when amply supplied with reducing power in the form of NADPH, and to initiate down-regulation by acification of the thylakoid lumen.

The methods of the invention allow one or more photosynthetic parameters of a plant to be determined by measuring the steady-state turnover rates and resistances to turnover of photosynthetic reactions and protein complexes just after a rapid light-to-dark transition. The relaxation processes that occur just after switching off the light (i.e., the Dark Interval Relaxation Kinetics, abbreviated as DIRK) reflect the processes that occurred in the light, and thus the measurements provide information of the steady-state of photosynthesis. The physiological state of a plant (such as whether the plant is subject to an environmental stress) affects photosynthesis. Thus, the methods of the invention can be used to measure one or more photosynthetic parameters which, in turn, can be used to indicate the presence of one or more plant stresses before they become apparent as lowered crop yields or other visible symptoms.

The present invention also provides kinetic spectrophotometers that can be used, for example, in the methods of the invention to collect spectral data from a plant leaf, and the spectral data can be used to determine a value for a photosynthetic parameter. The kinetic spectrophotometers of the present invention utilize a compound parabolic concentrator (CPC) to direct light generated by a light source onto a sample. The CPC intensifies and diffuses the light from the light source before directing the light onto the sample. The ability of the CPC to intensify light permits the generation of high intensity, short-duration pulses of light, which yield high sensitivity signals. Further, when the kinetic spectrophotometers of the invention are utilized to measure a photosynthetic parameter in a plant leaf, the diffused light emerging from the CPC reduces the effects of light-scattering changes within the leaf.

Kramer and Sacksteder (Kramer D. M. and Sacksteder C. A., *Photosynthesis Research* 56: 103–112 (1998)) disclose a kinetic spectrophotometer that scatters collimated light from a xenon flashlamp before directing the scattered light onto a sample, such as a plant leaf. The light scattering is mainly achieved by passing the light through a hollow scattering chamber made from a material that efficiently scatters light. A substantial amount of the light entering the scattering chamber is lost, for example by escaping through the entry port leading into the light scattering chamber. Typically, less than fifty percent of the light entering the scattering chamber emerges therefrom and is available to be directed onto the sample. In contrast, in the kinetic spectrophotometers of the present invention, typically more than ninety five percent of light entering the CPC, disposed between the light source and the sample, emerges from the CPC and is available to be directed onto the sample.

SUMMARY OF THE INVENTION

In one aspect, the present invention provides kinetic spectrophotometers that each comprise: (a) a light source; and (b) a compound parabolic concentrator disposed to receive light from the light source and configured to (1) intensify and diffuse the light received from the light source, and (2) direct the intensified and diffused light onto a sample.

One embodiment of the kinetic spectrophotometers of the invention comprises: (a) a light source; (b) a compound parabolic concentrator comprising an entry aperture, defining an entry aperture area, and an exit aperture, defining an exit aperture area, wherein the compound parabolic concentrator is (1) disposed to receive light from the light source through the entry aperture; and (2) is configured to intensify and diffuse the light received from the light source, and to direct the intensified and diffused light, through the exit aperture, onto a sample, wherein the entry aperture area is larger than the exit aperture area; (c) a second compound parabolic concentrator comprising an entry aperture, defining an entry aperture area, and an exit aperture, defining an exit aperture area, wherein the second compound parabolic concentrator is (1) disposed to receive, through the entry aperture, light that is transmitted through the sample, or that is emitted by the sample; and (2) that is configured to collimate the received light, and to emit the collimated light through the exit aperture onto a filter, wherein the second compound parabolic concentrator entry aperture area is smaller than the second compound parabolic concentrator exit aperture area; (d) a filter disposed to receive light that is emitted from the second compound parabolic concentrator exit aperture, and that is adapted to block a portion of the light emitted from the second compound parabolic concentrator; and (e) a third compound parabolic concentrator comprising an entry aperture, defining an entry aperture area, and an exit aperture, defining an exit aperture area, wherein the third compound parabolic concentrator is (1) disposed to receive, through the entry aperture, light that passes through the filter; and (2) that is configured to intensify and diffuse the light received from the filter, and to direct the intensified and diffused light onto a light detector, wherein the third compound parabolic concentrator entry aperture area is larger than the third compound parabolic concentrator exit aperture area.

In other aspects, the present invention provides methods for measuring a photosynthetic parameter, the methods comprising the steps of: (a) illuminating a plant leaf until steady-state photosynthesis is achieved; (b) subjecting the illuminated plant leaf to a period of darkness; (c) using a kinetic spectrophotometer of the invention to collect spectral data from the plant leaf treated in accordance with steps (a) and (b); and (d) determining a value for a photosynthetic parameter from the spectral data.

The determined photosynthetic parameter(s) can be used to provide information about the type and amount of photosynthetic activity in a plant leaf, or in a whole plant, or population of plants. Additionally, the determined photosynthetic parameter(s) can be used to ascertain whether the subject plant is experiencing one or more of a variety of environmental and/or physiological stresses, such as temperature stress, drought stress and nutrient stress (including nitrogen stress). Thus, in one aspect, the present invention provides methods for determining the physiological state of a plant comprising: (a) illuminating a plant leaf until steady-state photosynthesis is achieved; (b) subjecting the illuminated plant leaf to a period of darkness; (c) using a kinetic spectrophotometer of the invention to collect spectral data from the plant leaf treated in accordance with steps (a) and (b); (d) determining a value for a photosynthetic parameter from the spectral data; and (e) using the determined value for the photosynthetic parameter to determine the physiological state of the plant.

The kinetic spectrophotometers of the invention are useful, for example, in the practice of the methods of the invention. Additionally, the kinetic spectrophotometers of the invention are useful, for example, to measure the absolute rates of photosynthetic productivity since the initial rates of decay of the electrochromic shift upon a rapid light to dark transition is proportional to the amount of ATP synthesized. The vast majority of ATP is utilized to fix $CO_2$, and so the initial rate of decay of the electrochromic shift should be a good approximation of the rate of $CO_2$ fixation. Further, the kinetic spectrophotometers of the invention are useful to measure any process that requires high sensitivity measurements of absorbance changes in highly scattering samples, or in samples which display large changes in light scattering (e.g., any assay using intact cells or sub-cellular organelles, or in rapid mixing experiments, such as stopped flow experiments).

BRIEF DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION OF THE PREFERRED EMBODIMENT

Figure 1:
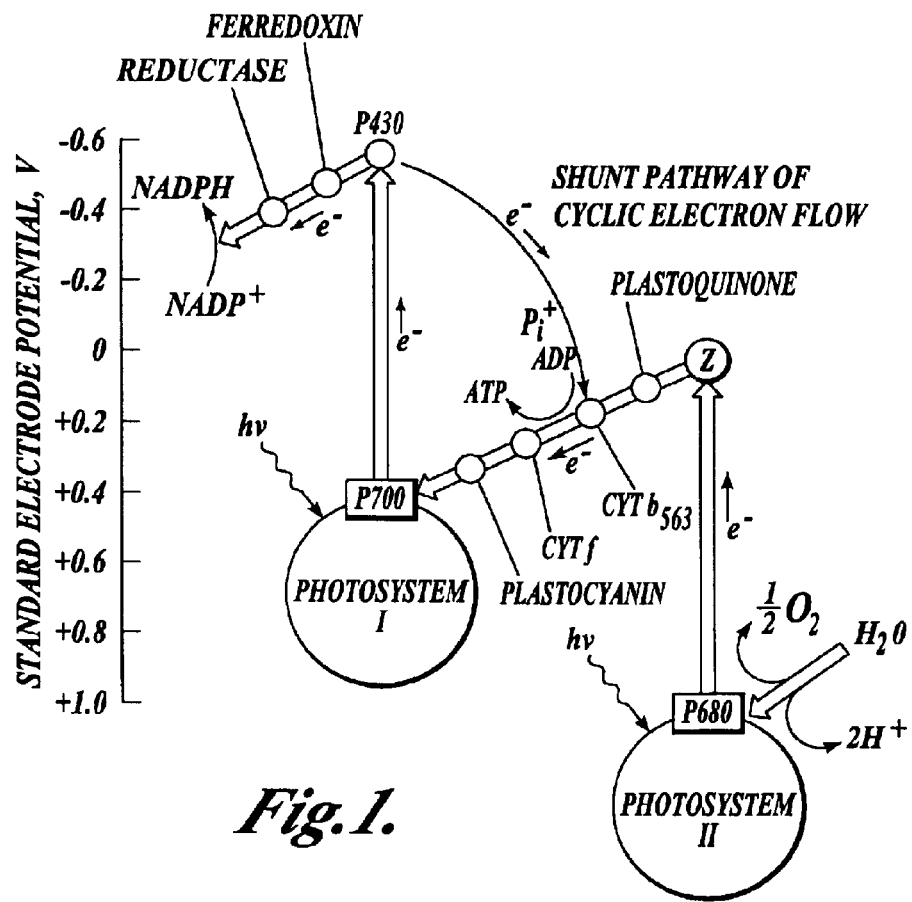
FIG. 1 shows the Z-scheme of electron transfer in the light reaction of photosynthesis.
Figure 2:
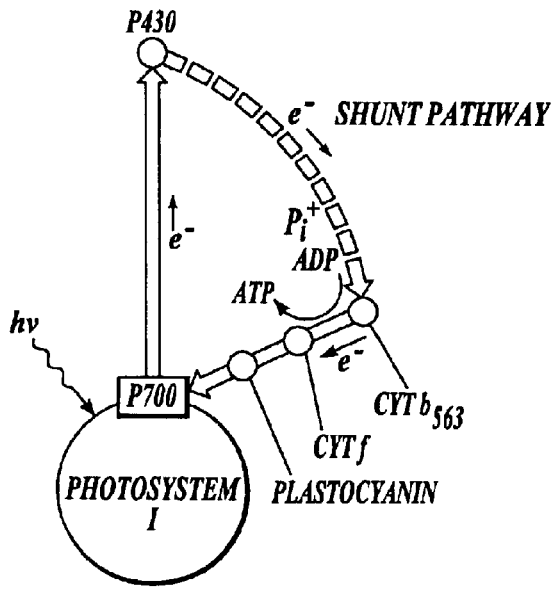
FIG. 2 shows cyclic electron flow in the light reaction of photosynthesis.

As used herein, the term "kinetic spectrophotometer" refers to an instrument capable of measuring changes in the light absorbance and/or changes in the fluorescent radiation emission of a sample (such as a plant leaf) over time.

As used herein, the term "steady-state photosynthesis" means that the concentrations of photosynthetic intermediates in the light reactions of photosynthesis are not changing significantly over the time scale of the period during which one or more photosynthetic parameters are being measured using the methods of the present invention. For example, if the concentrations of photosynthetic intermediates in the light reactions of photosynthesis do not change significantly over the time scale of one second, this state would be considered "steady-state photosynthesis" in the context of using the methods of the invention to measure electron transfer during a time period of 10 milliseconds.

As used herein the term "photosynthetic parameter" refers to any photosynthetic reaction that can be quantitatively measured using a kinetic spectrophotometer. Representative examples of photosynthetic parameters include: light-driven fluxes of protons through photosystems I and II, the levels of light-driven ATP synthesis, the control of light capture by the antenna complexes, the storage of proton motive force across the thylakoid membrane (both as an electric field and as a difference in pH values), and the redox states of the electron transfer components in the light and dark.

As used herein in connection with a CPC, the term "intensify" means the process of increasing the flux density of photons per unit area.

As used herein in connection with a CPC, the term "collimate" means the process of making the paths of all, or substantially all, photons passing through the CPC parallel.

As used herein in connection with a CPC, the term "diffuse" refers to the ability of the CPC to change the paths of photons entering the CPC so that most of the photons (i.e., greater than 95%) emerging from the CPC do not travel along parallel pathways.

The following abbreviations are used: $\phi_{II}$—quantum efficiency of PS II; A—$CO_2$ assimilation; CEF—cyclic electron flux; CPC—compound parabolic concentrator; cyt—cytochrome; DIRK—dark-interval relaxation kinetics; IR—infrared; LED—light-emitting diode; LEF—Linear electron flux; $P_{700}$—the primary chlorophyll electron donor of photosystem I; ms—millisecond; PS I—photosystem I; PS II—photosystem II; PC—plastocyanin; UV—ultra violet.

In one aspect, the present invention provides kinetic spectrophotometers that each include (a) a light source; and (b) a compound parabolic concentrator disposed to receive light from the light source and configured to (1) intensify and diffuse the light received from the light source, and (2) direct the intensified and diffused light onto a sample, such as a plant leaf.

A compound parabolic concentrator (CPC) is a nonimaging optical device that can intensify incident light energy so as to emit light energy that is more intense, and also more diffuse, than the light energy that entered the CPC. In design, a CPC is a skewed parabola rotated 360° around its long axis, and may be hollow or solid. A CPC includes two apertures, one aperture having a larger area than the other aperture, through which light can enter or leave the CPC. When light impinges on the larger aperture, the CPC concentrates the incident light at the larger (input) aperture to a more intense light beam at the smaller (output) aperture. The light leaving the smaller aperture is, however, more diffuse than the light entering the larger aperture. Conversely, light impinging on the smaller aperture is collimated by the CPC and exits from the larger aperture as less intense and less diffuse light energy.

The kinetic spectrophotometers of the invention include a CPC disposed to receive light from a light source and configured to (1) intensify and diffuse the light received from the light source, and (2) direct the intensified and diffused light onto a sample, such as a plant leaf. Thus, when the kinetic spectrophotometers of the invention are utilized in the methods of the invention to measure a photosynthetic parameter in a plant leaf, the aforesaid CPC directs onto the plant leaf a burst of light of one or more desired wavelengths that is, or are, preferentially or exclusively absorbed by one or more target component(s) of the photosynthetic apparatus, thereby yielding information about the target component(s). The ability of the aforesaid CPC to concentrate light permits the generation of high intensity, short-duration pulses of light, thus yielding high sensitivity signals. Further, the diffused nature of the light emerging from the CPC reduces the effects of light-scattering changes within the leaf sample.

Figure 3:
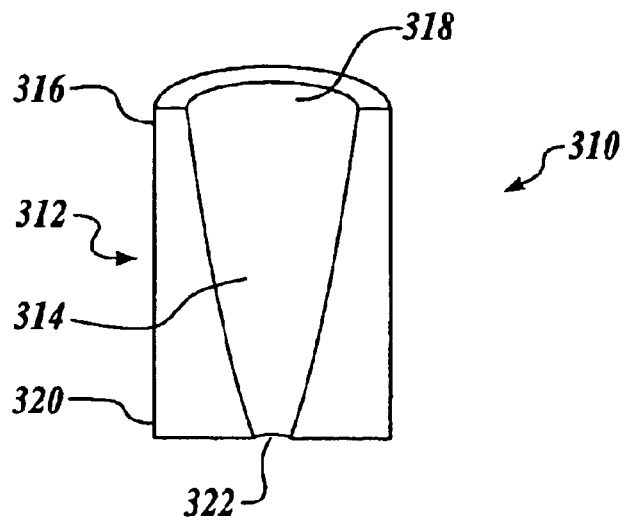
FIG. 3 shows a cross-sectional view of an exemplary, hollow, compound parabolic concentrator.

The CPCs useful in the kinetic spectrophotometers of the invention can be hollow or solid. Hollow CPCs reflect light within the hollow CPC body, while solid CPCs refract light that enters the solid CPC body. FIG. 3 shows a cross-sectional view of an exemplary, hollow, CPC 310 that includes a body 312 defining a cavity 314, a first end 316 defining a first aperture 318 and a second end 320 defining a second aperture 322. The area of first aperture 318 is larger than the area of second aperture 322. In the context of a hollow CPC, the term "aperture" refers to an opening in body 312 that permits light to enter or leave cavity 314.

Figure 4:
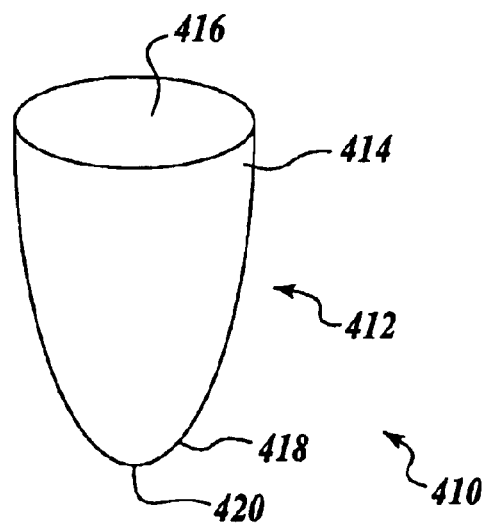
FIG. 4 shows a perspective view of an exemplary, solid, compound parabolic concentrator.

FIG. 4 shows a perspective view of an exemplary, solid, CPC 410 that includes a solid body 412 defining a first end 414 defining a first aperture 416 and a second end 418 defining a second aperture 420. The area of first aperture 416 is larger than the area of second aperture 420. In the context of a solid CPC, the term "aperture" refers to the portion of first end 414 or second end 418 through which light enters or leaves body 412.

When the kinetic spectrophotometers of the invention are utilized in the methods of the invention to measure a photosynthetic parameter in a plant leaf, hollow CPC 310 is preferable because cavity 314 facilitates exchange of gases to and from the leaf.

The light source can be any suitable light source, such as an array of light emitting diodes (LEDs). Other useful light sources include, for example, incandescent lights, arc lamps, xenon flash lamps, pulsed lasers, or laser diodes with outputs in the appropriate spectral regions. Pulsed signals are preferred. An array of LEDs has the advantage that it can be configured to emit different wavelengths of light. For example, when the kinetic spectrophotometers of the invention are utilized in the methods of the invention to measure a photosynthetic parameter in a plant leaf, some diodes in an array of LEDs can be configured to emit actinic light that energizes all, or substantially all, of the light reactions of photosynthesis, thereby stimulating the leaf to achieve steady-state photosynthesis. Other diodes in the same array of LEDs can be configured to emit light of one or more desired wavelength(s) that is preferentially or exclusively absorbed by one or more targeted component(s) of the photosynthetic apparatus, thereby yielding information about the targeted component(s).

Figure 5:
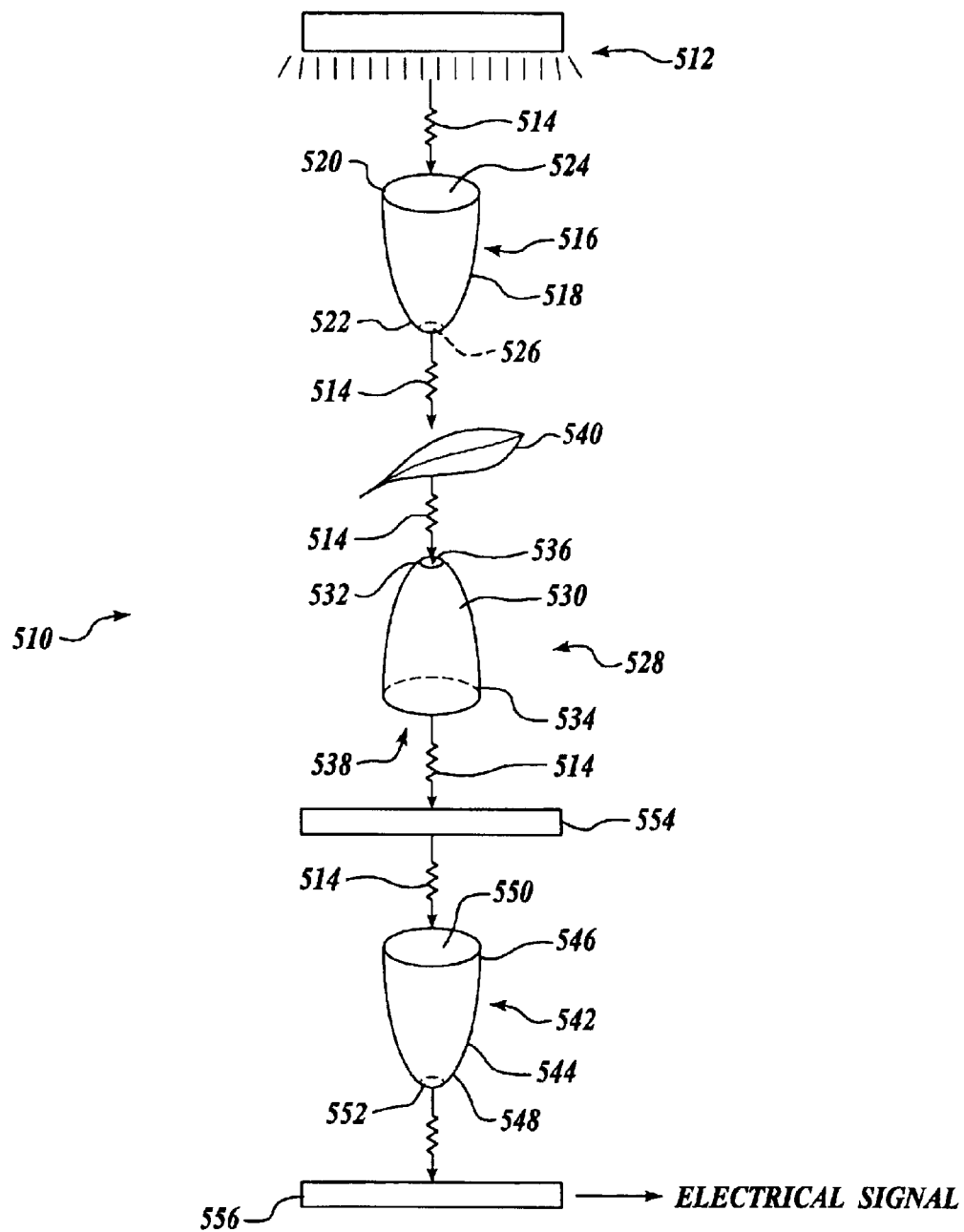
FIG. 5 shows a schematic representation of a kinetic spectrophotometer of the invention.

FIG. 5 shows a representative example of a kinetic spectrophotometer 510 of the present invention. Kinetic spectrophotometer 510 includes a light source 512, such as an array of light emitting diodes, that produces a beam of light 514, that includes actinic light wavelengths and one or more measuring light wavelength(s), and a first compound parabolic concentrator (CPC) 516 that includes a body 518 defining a proximal end 520 and a distal end 522. Proximal end 520 of body 518 defines an entry aperture 524, and distal end 522 of body 518 defines an exit aperture 526. The area of entry aperture 524 is greater than the area of exit aperture 526, and entry aperture 524 is closer to light source 512 than exit aperture 526.

Kinetic spectrophotometer 510 also includes a second CPC 528 that includes a body 530 defining a proximal end 532 and a distal end 534. Proximal end 532 of body 530 defines an entry aperture 536 and distal end 534 of body 530 defines an exit aperture 538. The area of entry aperture 536 is smaller than the area of exit aperture 538, and entry aperture 536 is closer to distal end 522 of first CPC 516 than is exit aperture 538. In operation, a sample 540 (a leaf in FIG. 5) is disposed between distal end 522 of first CPC 516 and proximal end 532 of second CPC 528.

Kinetic spectrophotometer 510 further includes a third CPC 542 that includes a body 544 defining a proximal end 546 and a distal end 548. Proximal end 546 of body 544 defines an entry aperture 550 and distal end 548 of body 544 defines an exit aperture 552. The area of entry aperture 550 is greater than the area of exit aperture 552, and entry aperture 550 is closer to distal end 534 of second CPC 528 than is exit aperture 552. A light filter 554 is disposed between distal end 534 of second CPC 528 and proximal end 546 of third CPC 542.

Kinetic spectrophotometer 510 also includes a light detector 556, such as a photodiode. In the embodiment of kinetic spectrophotometer 510 shown in FIG. 5, each of first CPC 516, second CPC 528 and third CPC 542 are hollow, but each of first CPC 516, second CPC 528 and third CPC 542 can be solid.

In operation, light beam 514 is emitted by light source 512 and enters first CPC 516 through entry aperture 524. Light beam 514 is intensified and diffused within body 518 of first CPC 516, and leaves first CPC 516 through exit aperture 526. Light beam 514 then impinges on sample 540 (a plant leaf in FIG. 5). The portion of light beam 514 that is not absorbed by sample 540 enters second CPC 528 through second CPC entry aperture 536. It will be understood that sample 540 can also emit light in the form of fluorescence which forms a part or all of the wavelengths present in light beam 514 after light beam 514 impinges on sample 540.

Light within second CPC 528 is collimated and exits second CPC 528 through exit aperture 538 and then passes through light filter 554 which removes undesirable wavelengths within light beam 514, but permits the passage of desired light wavelength(s) within light beam 514. Light beam 514 passing through filter 554 enters third CPC 542 through entry aperture 550 and is intensified and diffused by third CPC 542 before passing through exit aperture 552 and impinging upon light detector 556, such as one or more photodiodes. Light detector 556 converts impinging light beam 514 to an electrical signal that can be stored and analyzed.

The embodiment of kinetic spectrophotometer 510 shown in FIG. 5 is capable of generating a pulsed light beam 514 that permits high sensitivity (typically <100 ppm noise) and time resolution (about 10 microseconds) in the visible and near infrared spectral regions.

In another aspect, the present invention provides methods for measuring a photosynthetic parameter, the methods include the steps of: (a) illuminating a plant leaf until steady-state photosynthesis is achieved; (b) subjecting the illuminated plant leaf to a period of darkness; (c) using a kinetic spectrophotometer of the present invention to collect spectral data from the plant leaf treated in accordance with steps (a) and (b); and (d) determining a value for a photosynthetic parameter from the spectral data.

Typically, the illuminated plant is subjected to darkness for a period of from 2 milliseconds to 120 seconds, depending on the photosynthetic process that is being measured. It will be understood that the plant subjected to darkness is nonetheless illuminated (for at least a portion of the dark period) by one or more measuring beams of light generated by the kinetic spectrophotometer. Depending upon the wavelength(s) of the measuring beam(s), many processes can be measured by their absorbance of light, which can be expressed as the differences in transmission normalized to a standard transmission ($\Delta I/I_0$). Wavelength of light is measured in units of nanometers (nm).

Thus, in one embodiment, kinetic spectrophotometer 510, including an array of light emitting diodes as light source 512, can be used to illuminate a plant leaf until steady-state photosynthesis is achieved, then to subject the illuminated plant leaf to a period of darkness by switching off the light emitting diodes, and then directing a beam of measuring light of defined wavelength(s) onto the leaf in order to collect spectral data (such as the amount of a specific photosynthetic component that specifically absorbs the measuring light wavelength(s)). The array of light emitting diodes can be configured to include diodes that emit actinic light that stimulates the plant leaf to achieve steady-state photosynthesis, and also to include diodes that emit measuring light of desired wavelength(s).

Data collected using the methods of the present invention show the relaxation of absorbance changes upon briefly shuttering actinic light impinging on a plant leaf. The initial changes reflect what occurred just prior to shutter closure. It is difficult to measure fluxes through a process in the steady-state because the concentrations of reaction intermediates (i.e., what is being measured) do not change. The steady-state must be disturbed to measure it. The inventive methods do this in a non-invasive way, by inhibiting only the light-driven reactions, and following the progress (or relaxation) of one or more of the non-light driven reactions, in plant photosynthesis.

Figure 6:
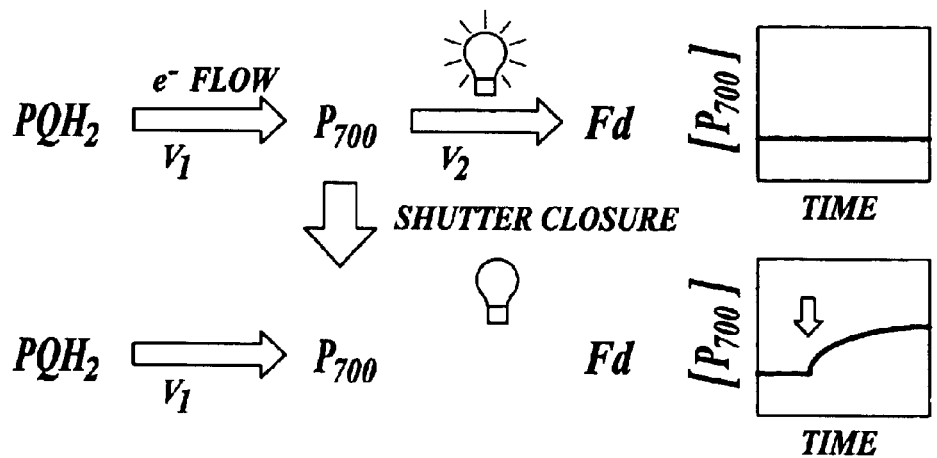
FIG. 6 shows a schematic diagram of the methods of the present invention as applied to the measurement of the steady-state turnover of PS I ($P_{700}$).

By way of example, FIG. 6, shows how the methods of the invention can be used to measure the steady-state turnover of PS I ($P_{700}$). In the steady-state, the rate of light-driven oxidation of $P_{700}$ ($v_2$) is precisely counterbalanced by the rate of its rereduction via turnover of the cytochrome $b_6f$ complex ($v_1$), leading to a stable $P_{700}$ redox state. By briefly and rapidly shuttering the light, $v^2$ is temporarily inhibited, thus allowing the system to relax. The initial changes in the concentration of reduced $P_{700}$ (the dark relaxation) reflect $v_1$, and are proportional to the flux through the system just prior to the shuttering. It should be noted that the methods of the present invention are not sensitive to changes in the PS I acceptor side redox state (see, Klughammer C and Schreiber U *Planta* 192: 261–268 (1994)) when used to measure PS I flux, and so should be free from this potential artifact.

Representative examples of photosynthetic parameters that can be determined using the methods of the invention are: one or more redox reactions of the photosystem I primary electron donor (the required spectral data can be obtained, for example, by illuminating the plant leaf with a measuring beam of light having a wavelength of 703 nm, or a wavelength in the range of 800–850 nm); one or more redox reactions of plastocyanin (the required spectral data can be obtained, for example, by illuminating the plant leaf with a measuring beam of light having a wavelength of 600 nm, or a wavelength in the range of 850–925 nm); one or more redox reactions of cytochrome f (the required spectral data can be obtained, for example, by illuminating the plant leaf with a measuring beam of light having a wavelength selected from the group consisting of 435, 545, 554 and 560 nm); one or more redox reactions of cytochrome b (the required spectral data can be obtained, for example, by illuminating the plant leaf with a measuring beam of light having a wavelength selected from the group consisting of 420, 563 and 572 nm); one or more redox reactions of the primary quinone acceptor of photosystem II (the required spectral data can be obtained, for example, by illuminating the plant leaf with a measuring beam of light having a wavelength of 300 nm, or a wavelength selected from the group consisting of 545, 550 and 555 nm (which measures the Stark-shift of the nearby pheophytin)); the conversion of violaxanthin to antheraxanthin and zeaxanthin (in response to thylakoid lumen acidification) in the light harvesting complexes (the required spectral data can be obtained, for example, by illuminating the plant leaf with a measuring beam of light having a wavelength of 505 nm); the amount of energy stored across the thylakoid membrane (the required spectral data can be obtained, for example, by illuminating the plant leaf with a measuring beam of light having a wavelength selected from the group consisting of 470 and 520 nm); and the fraction of open photosystem II reaction centers (the required spectral data can be obtained, for example, by illuminating the plant leaf with a measuring beam of light having a wavelength greater than 650 nm).

Additional examples of photosynthetic parameters that can be determined from the spectral data obtained from plant leaves treated in accordance with the methods of the invention include: electron ($e^-$) transfer through photosystem I; electron ($e^-$) transfer through photosystem II; the quantum efficiency of the photosystem I and II antennae complexes; proton transfer across the thylakoid membrane; the percentage of electron transfer going through the cyclic pathway; the percentage of electron transfer going through the linear pathway (the so-called Z-scheme); the amplitude of the electrochromic shift (which is an indication of the amount of energy stored across the thylakoid membrane as proton motive force); and the chlorophyll content.

Example 4 herein shows the use of kinetic spectrophotometer 510 to measure electrochromic shift decay kinetics in tobacco leaves. Additionally, Example 5 herein shows the use of kinetic spectrophotometer 510 to compare relative proton fluxes, estimated by $DIRK_{ECS}$, using broadband 525 nm LEDs light as a measuring beam, with PS II electron flux, estimated by the saturation-pulse fluorescence rise technique.

In addition to absorbance, changes in the chlorophyll fluorescence of plants, measured at wavelengths greater than 650 nm, can yield important information about the state of the photosynthetic apparatus. Photons of light absorbed by pigments in the light harvesting complexes are called excitons. Excitons can decay by several pathways, the most prominent being photochemistry in the reaction centers, fluorescence, non-radiative decay (to heat) and the formation of triplet states (intersystem crossing). The rates of exciton decay down these pathways are modulated by the state of the chloroplast. When the photosystem II reaction centers are active (i.e. in 'open' states) most excitons are delivered to them, and used for performing photochemistry. When the photosystem II centers are closed, excitons decay by other routes, such as fluorescence. The increased flux of excitons through the fluorescence decay pathway is then an indicator that photosystem II reaction centers are in inactive states.

During normal photosynthesis, photosystem II reaction centers are excited by light, and pass through several inactive, highly fluorescent states before returning to open states that can accept more light energy. When the input of light energy is high, the input of excitons into the reaction centers competes with the return to open states and the fraction of photosystem II centers in closed states increases, increasing the fraction of excitons that decay through fluorescence. By analyzing fluorescence yield, the fraction of open photosystem II reaction centers can be estimated. In addition, the rate of photosystem II center reopening can be observed by measuring the kinetics of decay of highly fluorescent states after light exposure.

The major processes that downregulate photosynthesis decrease the fraction of excitons that reach the reaction centers. This is accomplished by "shunting" excitons to heat, via non-radiative processes, and thus these processes are collectively termed non-photochemical quenching (NPQ) of excitation energy. The activation of NPQ affects fluorescence because the quenching process also competes with the decay of excitons to fluorescence. Thus, the maximal fluorescence when all reaction centers are closed, decreases when downregulation is activated.

A representative way of determining electron transfer through the cytochrome $b_{6f}$ complex and photosystem I from spectral data collected from a plant leaf is as follows. The absorbance signal at around 820–830 nm reflects the redox state of the primary electron donor of photosystem I, the pair of chlorophylls termed $P_{700}$. Thus, the initial rate of change of the 820 nm signal (measured by taking a best fit line through the first few milliseconds of the curve) provides an estimate of the rate of electron transfer through photosystem I and the cytochrome $b_{6f}$ complex. The total extent of the 820 nm signal during the dark period of the DIRK measurement is taken as an indicator of the redox state of $P_{700}$ during illumination. The time required for the 820 nm signal to decay from the steady state light value to half of the dark value is the half time. The more resistance to flux, the longer is the half time.

A representative way of determining the flux of protons through the photosynthetic apparatus from spectral data collected from a plant leaf is as follows. In the light, protons are pumped from the stroma to the lumen of the chloroplast. The protons then pass through the ATP synthase, forcing the formation of ATP which, in turn, powers the fixation of $CO_2$ as well as other important cellular processes. During steady state photosynthesis, protons are pumped in at the same rate that they pass through the ATP synthase. Abruptly cutting the light inhibits the movements of protons into the lumen, but does not immediately halt their efflux through the ATP synthase. The net efflux of protons affects the electric field across the thylakoid membrane. A kinetic spectrophotometer of the invention can be used to follow this process by measuring the absorbance signal that is indicative of the changes in the electrical field, namely the electrochromic shift, a broad absorbance signal at around 520 nm (any wavelength from about 510 nm to 535 nm can be used to measure the electrochromic shift). The initial rate of change of the electrochromic shift signal, measured over the first 10–20 milliseconds, reflects the rate of proton flux through the photosynthetic apparatus and the ATP synthase. The half time (measured as the time required for the electrochromic shift to relax to half the full extent in the dark) is taken as a measure of the resistance or impedance to flux. The full extent of the electrochromic shift signal reflects the degree of energization of the thylakoid membrane in the light.

A representative way of determining electron transfer through photosystem II from spectral data collected from a plant leaf is as follows. Under physiological conditions, the yield of fluorescence from antenna chlorophylls associated with photosystem II is sensitive to two main factors: (1) the redox state of the primary photosystem II quinone electron acceptor $Q_A$, and (2) the degree of downregulation of the photosynthetic apparatus, which results in shunting light energy to heat. This process will also divert light energy from fluorescence. It is possible to estimate both the extent of downregulation and the rate of photosynthesis from chlorophyll fluorescence yield changes. The rate of photosystem II electron transfer can be measured by applying supersaturating pulses of actinic light (typically one second of greater than 10,000 mol photons $m^{-2} s^{-1}$ of white lights). These pulses act to saturate (and therefore close) all photosystem II centers. In this condition, all quenching (or reduction) of fluorescence by photochemistry is inhibited. The saturating pulse-induced rise in fluorescence is used as an indicator of the quantum yield of photosystem II photochemistry, $\phi_{II}$, as:

$$\phi_{II} = (F_s - F_{m'})/F_{m'} \qquad (1)$$

where $F_s$ is the steady state fluorescent yield, and $F_{m'}$ is the fluorescence yield measured during the saturating pulse.

The rate of photosynthesis is estimated by multiplying $\phi_{II}$ by the absorbed light intensity, I. The extent of downregulation is estimated by a parameter called non-photochemical quenching, or NPQ, which is usually calculated as:

$$NPQ = (F_m - F_{m'})F_{m'} \qquad (2)$$

where $F_m$ is the maximum fluorescence yield measured during a saturating pulse in dark-adapted material, when no NPQ is present.

Photosynthetic parameter(s) measured in accordance with the present invention can be used to determine whether the subject plant is experiencing one or more of a variety of environmental and/or physiological stresses, such as temperature stress, drought stress and nutrient stress (including nitrogen stress). Thus, in one aspect, the present invention provides methods for determining the physiological state of a plant comprising: (a) illuminating a plant leaf until steady-state photosynthesis is achieved; (b) subjecting the illuminated plant leaf to a period of darkness; (c) using a kinetic spectrophotometer of the present invention to collect spectral data from the plant leaf treated in accordance with steps (a) and (b); (d) determining a value for a photosynthetic parameter from the spectral data; and (e) using the determined value for the photosynthetic parameter to determine the physiological state of the plant. In one embodiment, the step of using the determined value for the photosynthetic parameter to determine the physiological state of a plant comprises the step of comparing the determined value for the photosynthetic parameter to a reference value for the same photosynthetic parameter determined from spectral data obtained from one or more reference plants. Typically a difference is observed between the determined value for the photosynthetic parameter and the reference value for the photosynthetic parameter. The difference can typically be correlated with the presence of a physiological stress in the plant.

For example, utilizing the foregoing methods for determining the physiological state of a plant, changes in the following, representative, photosynthetic parameters can be correlated with the presence of a physiological stress in a plant: an increase in electron transfer through photosystem I (relative to electron transfer through photosystem I in one or more reference plants) is correlated with the presence of heat stress in the plant; an increase in the electrochromic shift (relative to the electrochromic shift in one or more reference plants) is correlated with the presence of heat stress in the plant; an increase in chlorophyll a fluorescence (relative to chlorophyll a fluorescence in one or more reference plants) is correlated with the presence of heat stress in the plant; an increase in the ratio of the amplitudes of 820 nm absorbance and 525 nm absorbance (relative to the ratio of the amplitudes of 820 nm absorbance and 525 nm absorbance in one or more reference plants) is correlated with the presence of drought stress in the plant; an increase in ATP synthase activity (relative to ATP synthase activity in one or more reference plants) is correlated with the presence of drought stress in the plant; an increase in $P_{700}$ reduction (relative to $P_{700}$ reduction in one or more reference plants) is correlated with the presence of drought stress in the plant; an increase in the proton/electron resistance ratio (relative to the proton/electron resistance ratio in one or more reference plants) is correlated with the presence of drought stress in the plant; a decrease in ATP synthase activity (relative to ATP synthase activity in one or more reference plants) is correlated with the presence of nitrogen stress in the plant; a decrease in $P_{700}$ reduction (relative to $P_{700}$ reduction in one or more reference plants) is correlated with the presence of nitrogen stress in the plant; a decrease in the proton/electron resistance ratio (relative to the proton/electron resistance ratio in one or more reference plants) is correlated with the presence of nitrogen stress in the plant.

The following examples merely illustrate the best mode now contemplated for practicing the invention, but should not be construed to limit the invention.

EXAMPLE 1

This example describes the materials and kinetic spectrophotometer used to produce the data described in Examples 2–5.

Plant Material: *Nicotiana tobacum* (tobacco) plants were started in a growth chamber with a 16/8 h day/night cycle, ~350 μmol photons $m^{-2}$ $s^{-1}$ light intensity, air temperature of 28/18° C. and a relative humidity of 80%. At two weeks they were transferred to a greenhouse setting where light intensity reached a maximum of ~900 μmol photons $m^{-2}$ $s^{-1}$. The plants were watered and fertilized as needed. The young, fully expanded, attached leaves were used from plants that ranged from 4 to 5 weeks old for all experiments.

Kinetic Spectrophotometer: kinetic spectrophotometer 510 shown in FIG. 5 was utilized. Each of first CPC 516, second CPC 528 and third CPC 542 were made from polished aluminum. Both measuring and actinic light were provided by banks of light emitting diodes (LEDs), with integral lenses, producing a cone of light with a 15° dispersion angle. LEDs of three separate wavelengths (see below) were interspersed over a 3 cm diameter circuit board and aimed approximately in parallel into entry aperture 524 (3 cm diameter) of first CPC 516. The acceptance angle ($\theta_i$) of entry aperture 524 was 20°, giving essentially greater than 90% transmission for rays entering entry aperture 524 at less than 19°. Light exiting exit aperture 526 (ca. 6 mm diameter) of first CPC 516, was diffused and approximately 10-fold intensified. At this point, the light struck sample leaf 540.

Filter 554 was housed within a filter wheel, computer controlled through a servomotor (CS-26 BB, Cirrus, Fremont, Calif.). Light passing through filter 554 was concentrated by third CPC 542, with entry aperture 550 and exit aperture 552 of 2 and 1 cm diameter, respectively. Light exiting third CPC 542 was detected by a 1 $cm^2$ surface silicon photodiode (S1337-1010BR, Hamamatsu, Japan) and converted to a voltage by a transimpedance amplifier (OPA027, Analog Devices, ). The amplified signal was then passed to a 16-bit data acquisition card (PC-CARD-DAS16/16, Computer Boards, Middleboro Mass.) for storage and analysis on the computer. Light pulse and data collection were timed by a series of digital timers on a computer card (PC-CARD-D24/CTR3, Computer Boards, Middleboro Mass.).

Kinetic spectrophotometer 510 was controlled by a program written in-house using Visual Basic 6.0 (Microsoft). The software selects the measuring beam of interest, the number of averages, time between traces, the length of each kinetic trace and the duration of the dark interval for the DIRK analysis. This information was sent to the counters on the input/output cards, which control the electronics for the modulation of the actinic light, pulsing of measuring LEDs and the collection of data. When accumulating averages, kinetic traces at multiple wavelengths were interleaved, ensuring an average response over the total duration of the experiment.

Absorbance changes were approximated by $-\Delta I/I_0$ (i.e., change in transmitted light over reference transmitted light), where $I_0$ was calculated from the average of baseline points. It was sometimes necessary to ignore the earliest baseline points to account for small changes in measuring beam intensity caused by heating of the LEDs.

Actinic light was provided by a bank of six high-intensity LEDs with dominant wavelengths of 644 nm (HLMP-C116, Hewlett Packard, Palo Alto Calif.). After passing through first CPC 516, the maximum measured intensity was ~1500 μmoles $m^{-2}$ $s^{-1}$. This intensity was stable within a few percent over the hours time scale. In addition to the six actinic LEDs, a separate bank of 12 LEDs were transiently overdriven (ca. 5 V across each diode) during the 750 ms saturation pulses, to produce either 5030 and 7070 μmol $m^{-2}$ $s^{-1}$ red light. It was estimated that these intensities were equivalent to white light pulses of about 7545 μmol $m^{-2}$ $s^{-1}$ and 10605 μmol $m^{-2}$ $s^{-1}$ (see, McCree K. J., Agric Meteorol 9: 191–216 (1972)).

The probe pulses for electrochromic shift measurements were supplied by high intensity green LEDs with dominant wavelength at 525 nm (HLMP-CB15, Hewlett Packard, Palo Alto, Calif.) full width half maximum (FWHM) of 49 nm. In some cases, ECS kinetics were obtained by passing this broadband light through a blue-green color glass blocking filter (BG18, Schott Glass). In other cases, spectral changes in the 500 nm to 550 nm region were resolved by passing the broadband light through a series of 3–5 nm interference filters (Omega Optical, Brattleboro, Vt.), mounted in the blocking filter holder.

Fluorescence was probed using an additional bank of three 644 nm LEDs as an excitation light. The photodiode detector 556 was protected from the probe pulses using a broadband interference filter (780BP120, Omega Optical, Brattleboro, Vt.), which also blocked infrared emission from the LEDs.

Measurements of steady-state absorbance change and Saturation-pulse Fluorescence: Relative steady-state proton fluxes were estimated using DIRK analysis of electrochromic shift (ECS) ($DIRK_{ECS}$) by measuring absorbance changes in the 500–545 nm spectral region. The DIRK initial rates were estimated as the apparent absorbance changes over the first 7.5 ms after a brief (125 ms) dark interval.

Estimates of relative proton to electron stoichiometry were taken at light intensities ranging from 188 $\mu$mol m$^{-2}$ s$^{-1}$ to 1500 $\mu$mol m$^{-2}$ s$^{-1}$. The plant was adapted to each light intensity for 15 minutes prior to the start of assays.

EXAMPLE 2

This example shows the sensitivity and time resolution ability of kinetic spectrophotometer 510 shown in FIG. 5 and described in Example 1.

Figure 7:
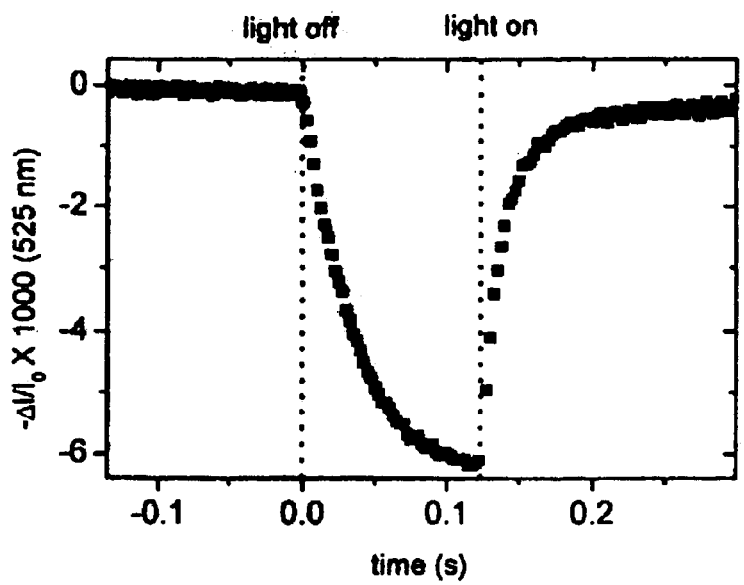
FIG. 7 shows the kinetics of absorbance changes, estimated as $-\Delta I/I_0$, at 525 nm in an intact tobacco leaf, during 125 ms dark intervals using the kinetic spectrophotometer shown in FIG. 5 and described in Example 1. The leaf was clamped in a leaf holder under 1083 μmol photons $m^{-2}$ $s^{-1}$ actinic light and adapted for a minimum of 15 min before initiation of the experiment. The trace shown is an average of 8 traces taken at 1.5 s intervals.

FIG. 7 shows a kinetic trace during a 125 ms dark interval, with the broadband 525 nm LED measuring light. A decay in absorbance occurred after the light-dark transition, with a half-time of about 25 ms. The noise level, taken as the standard deviation of baseline points, was 60 ppm, after 8 averages, which was sufficient for measurements of ECS. Traces taken with narrow band filtered light at 520 nm showed 5–10 fold higher noise levels, indicating that, in this mode, the sensitivity was limited by the intensity of the measuring pulses. The sensitivity of the instrument could be improved by using additional or brighter LEDs.

The amplitude of each measuring pulse was integrated by the electronic circuitry before data conversion, and thus the time resolution of the instrument was determined by the width of the LED pulses. In the experiment reported herein, kinetic spectrophotometer 510 provided square pulses with ca. 10 $\mu$s resolution. This is more than adequate to resolve the decay of the ECS, which occurs over the tens of ms time scale. Shorter or longer pulses, providing high time-resolution or sensitivity, respectively, could readily be implemented.

EXAMPLE 3

This example shows that kinetic spectrophotometer 510 minimizes the problem of interference from light scattering changes caused by sample 540.

Figure 8:
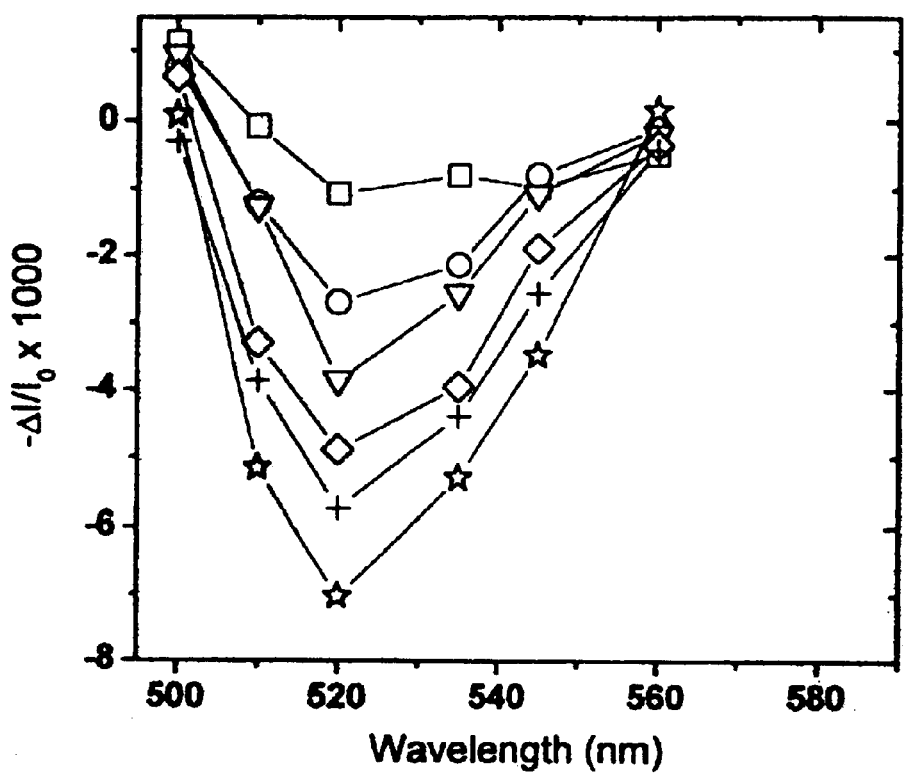
FIG. 8 shows resolved absorbance changes in the 500 to 560 nm region induced by punctuating continuous background light by a 125 ms dark interval in an intact tobacco leaf. Spectra are shown for 5 milliseconds (ms) (squares), 10 ms (circles), 12.5 ms (triangles), 22.5 ms (diamonds), 30 ms (crosses) and 125 ms (stars) after the light to dark transition. The conditions were as in FIG. 7 except that the broadband blocking filter was replaced with a series of narrow band (5 nm) interference filters, and 700 averages were taken at each wavelength indicated.

FIG. 8 shows absorbance changes that followed a 125 ms dark interval during continuous illumination. Since the ECS has a peak at ~518 nm, while light scattering shows a peak at ~535 nm (see review in Kramer D. M. and Sacksteder C. A., Photosynth. Res. 56: 103–112 (1998)), significant contributions from scattering would be observed as a pronounced shift in the spectrum towards longer wavelengths. The initial absorbance change, at 5–12.5 ms, was essentially as previously observed for pure ECS (Kramer and Sacksteder, supra). At all following time points the ratio of $-\Delta I/I_0$ at 535 and 525 nm remained constant at about 0.75, indicating that the spectrum was not significantly contaminated by light scattering changes over the 125 ms time scale. Furthermore, for the purpose of DIRK analysis, this data indicated that the spectral contributions at around 520 nm should be proportional to ECS.

EXAMPLE 4

This example shows the use of kinetic spectrophotometer 510 to measure electrochromic shift decay kinetics in tobacco leaves.

Figure 9:
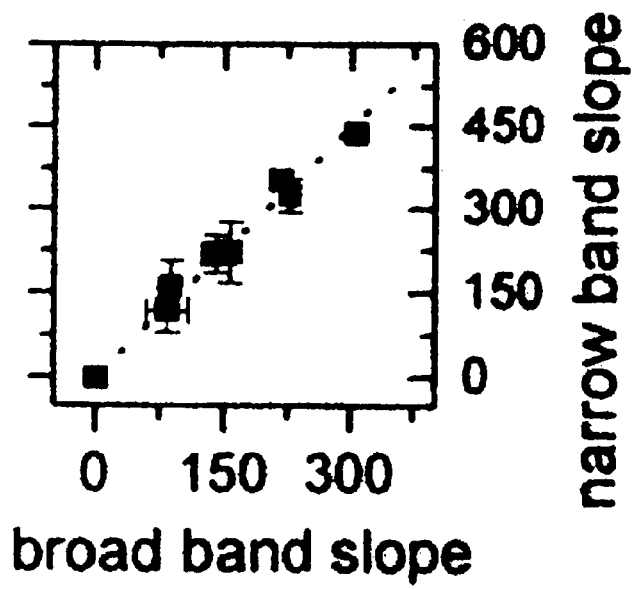
FIG. 9 shows a comparison of initial decay rates of the absorbance changes around 520 nm upon light-dark transitions determined using a broadband (525 nm LEDs filtered through color glass filter, Schott BG18, X-axis) and narrowband (LED light filtered through a 520 nm, 5 nm interference filter, Y-axis) measuring light. The units for both X and Y axes were $(-\Delta I/I_0 \times 1000)$ $s^{-1}$. The light intensity was varied from 188 to 1500 μmol photons $m^{-2}$ $s^{-1}$. The dotted line represents the best linear fit to the data, with an r-value of 0.991.

Absorbance measurements at 525 nm, taken with the broadband LED light, had significantly higher signal-to-noise ratios (and required 100-fold fewer averages) than did measurements taken with narrow band filtered light. We explored the possibility of using the broadband light directly as a linear indicator of ECS since the ECS constitutes by far the largest contributor to absorbance changes in the 500–545 nm range, and the ECS is quite broad (about 30 nm full width at half height). FIG. 9 shows that the initial rates of decay taken with the broadband LED light were proportional to those taken with the narrowband 520 nm light. As expected, the amplitudes of the slopes taken with the narrowband filter were larger (by ca. 1.4 times) than those taken with the broadband, since the latter also sampled changes on the edges of the absorbance spectrum. It was concluded that data taken with the broadband LED light was proportional to ECS, and thus could be used to estimate proton fluxes.

EXAMPLE 5

Figure 10:
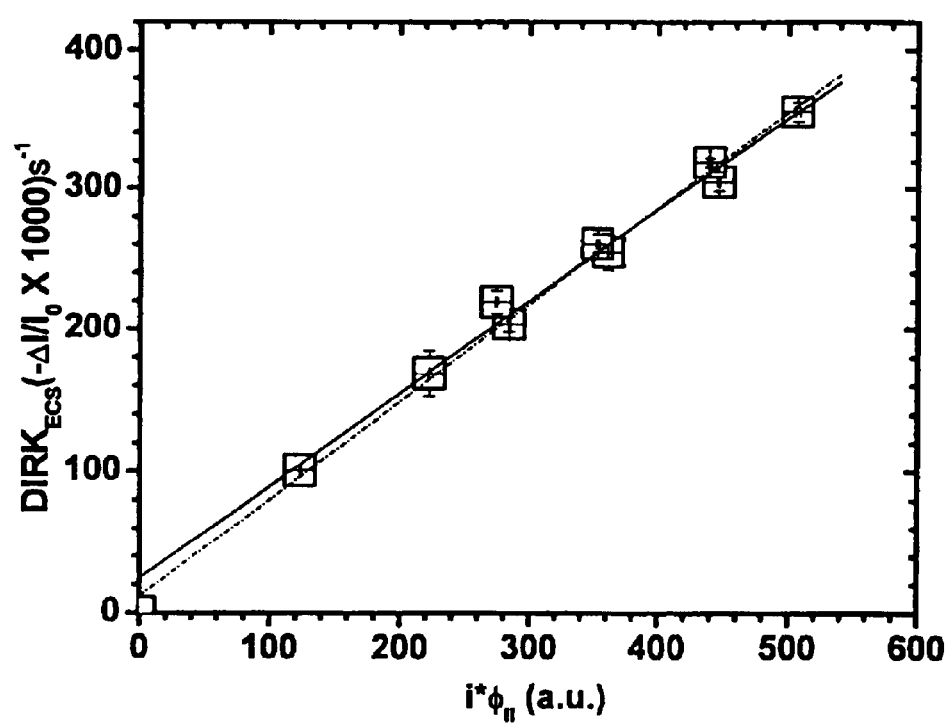
FIG. 10 shows relative $H^+/e^-$ ratios in an intact tobacco leaf, comparing proton flux through the ATP synthase with electron flux through PS II. The actinic light intensity was varied from 188 to 1500 μmol photons $m^{-2}$ $s^{-1}$. Estimates of relative proton fluxes were based on the initial rate of decay of the electrochromic shift ($DIRK_{ECS}$). Relative electron fluxes were estimated from the saturation pulse-induced changes in chlorophyll fluorescence yield. The solid and dashed lines represent the best linear fits excluding and including a point at the origin. The r-values for these two fits were essentially identical, at 0.995 and 0.996 respectively.

This example shows the use of kinetic spectrophotometer 510 to compare relative proton fluxes, estimated by $DIRK_{ECS}$, using broadband 525 nm LEDs light as a measuring beam, with PS II electron flux, estimated by the saturation-pulse fluorescence rise technique. FIG. 10 shows plots of i*$\phi$II or $DIRK_{ECS}$ versus light intensity which indicate that at the highest light intensity (1500 $\mu$mol photons m$^{-2}$ s$^{-1}$), photosynthesis was about 90% saturated (not shown). A linear relationship was observed between the narrow and broad band $DIRK_{ECS}$ analysis with an R=0.992. This result was consistent with earlier results obtained by the present inventors, and likely indicated a constant H$^+$/e$^-$ ratio for this leaf from low to nearly saturating light conditions.

EXAMPLE 6

This example shows the use of a kinetic spectrophotometer 510 of the present invention to identify heat stress in Concord grapes by measuring changes in the $P_{700}$ and electrochromic shift signals.

Heat stress is a major problem affecting many crops, particularly potato and some grape varieties. An effective indicator of heat stress can be used to direct remediation efforts, such as increasing irrigation. A rapid assay for heat damage would likely prove useful in breeding new potato varieties that are resistant to heat stress. Further, a knowledge of the severity of heat stress affecting a crop species could allow for a better estimate of crop loss, and could therefore be used to assess further market conditions for the crop.

Figure 11:
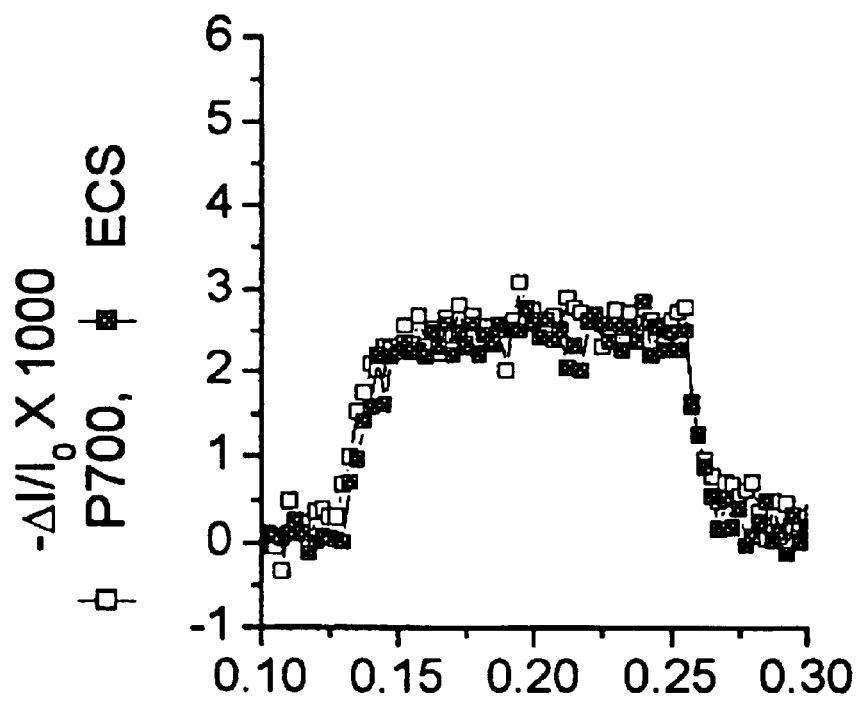
FIG. 11 shows the DIRK $P_{700}$ (open squares) and electrochromic shift (shaded squares) in Concord grapes on a cool day.
Figure 12:
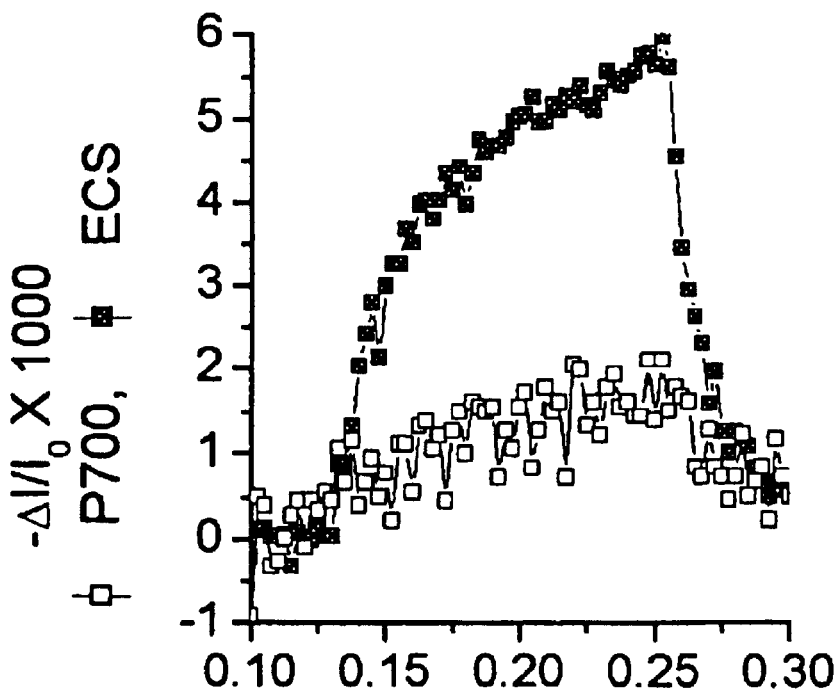
FIG. 12 shows the DIRK $P_{700}$ (open squares) and electrochromic shift (shaded squares) in Concord grapes on a hot day.

Concord grapes were grown at Washington State University's Killian fields. On each day of assay 15 data points were taken randomly within two rows of each pruning treatment. The field was irrigated with a furrow between each row. FIG. 11 shows DIRK measurements of $P_{700}$ and electrochromic shift on a cool day in July. FIG. 12 shows DIRK measurements of $P_{700}$ and electrochromic shift signals on a hot day (temperature of about 105° F.) in July. At high temperature the electrochromic shift signal increased, both in extent and in half time, indicating that the resistance to flux through the ATP synthase had increased. This resulted in an increase in steady state transthylakoid pH gradient. In contrast, the $P_{700}$ signal decreased, probably indicating Down regulation of photosynthesis as expected for a large transthylakoid pH gradient.

The increase in both half time and extent of the electrochromic shift signal is noteworthy because it indicates a slowing of the consumption of proton motive force at the ATP synthase. Further, it indicates that input of light energy into the reaction centers has probably exceeded the capacity of the photosynthetic apparatus to process it, probably resulting in long-term damage to the plant. Similar effects were noted in heat-sensitive potato (data not shown), but not in heat-resistant Merlot grapes (data not shown).

While the preferred embodiment of the invention has been illustrated and described, it will be appreciated that various changes can be made therein without departing from the spirit and scope of the invention.

The embodiments of the invention in which an exclusive property or privilege is claimed are defined as follows:

1. A kinetic spectrophotometer comprising:
   (a) a light source;
   (b) a compound parabolic concentrator comprising an entry aperture, defining an entry aperture area, and an exit aperture, defining an exit aperture area, wherein the compound parabolic concentrator is:
      (1) disposed to receive light from the light source through the entry aperture; and
      (2) is configured to intensify and diffuse the light received from the light source, and to direct the intensified and diffused light, through the exit aperture, onto a sample;
   wherein the entry aperture area is larger than the exit aperture area;
   (c) a second compound parabolic concentrator comprising an entry aperture, defining an entry aperture area, and an exit aperture, defining an exit aperture area, wherein the second compound parabolic concentrator is:
      (1) disposed to receive, through the entry aperture, light that is transmitted through the sample, or that is emitted by the sample; and
      (2) that is configured to collimate the received light, and to emit the collimated light through the exit aperture onto a filter;
   wherein the second compound parabolic concentrator entry aperture area is smaller than the second compound parabolic concentrator exit aperture area;
   (d) a filter disposed to receive light that is emitted from the second compound parabolic concentrator exit aperture, and that is adapted to block a portion of the light emitted from the second compound parabolic concentrator; and
   (e) a third compound parabolic concentrator comprising an entry aperture, defining an entry aperture area, and an exit aperture, defining an exit aperture area, wherein the second compound parabolic concentrator is:
      (1) disposed to receive, through the entry aperture, light that passes through the filter; and
      (2) that is configured to intensify and diffuse the light received from the filter, and to direct the intensified and diffused light onto a light detector;
   wherein the third compound parabolic concentrator entry aperture area is larger than the third compound parabolic concentrator exit aperture area.

2. A method for measuring a photosynthetic parameter comprising:
   (a) illuminating a plant leaf until steady-state photosynthesis is achieved;
   (b) subjecting the illuminated plant leaf to a period of darkness;
   (c) using a kinetic spectrophotometer to collect spectral data from the plant leaf treated in accordance with steps (a) and (b) wherein the kinetic spectrophotometer comprises;
      (1) alight source;
      (2) a compound parabolic concentrator disposed to receive light from the light source and configured to (1) intensify and diffuse the light received from the light source, and (2) direct the intensified and diffused light onto a sample; and
      (3) a light detector disposed to receive light that is transmitted through the sample, or that is emitted by the sample; and
   (d) determining a value for a photosynthetic parameter from the spectral data.

3. A method of claim 2 wherein the plant leaf is subjected to darkness for a period of time from 2 milliseconds to 120 seconds.

4. The method of claim 2 wherein the determined photosynthetic parameter is electron transfer through photosystem I.

5. The method of claim 4 wherein the spectral data is collected from the plant leaf by a method comprising illuminating the plant leaf with a measuring beam of light having a wavelength of 820 nm.

6. The method of claim 2 wherein the determined photosynthetic parameter is the electrochromic shift.

7. The method of claim 6 wherein the spectral data is collected from the plant leaf by a method comprising illuminating the plant leaf with a measuring beam of light having a wavelength of 525 nm.

8. The method of claim 2 wherein the determined photosynthetic parameter is chlorophyll a fluorescence.

9. The method of claim 8 wherein the spectral data is collected from the plant leaf by a method comprising illuminating the plant leaf with a measuring beam of light having a wavelength of 644 nm.

10. The method of claim 2 further comprising the step of using the determined value for the photosynthetic parameter to determine the physiological state of a plant.

11. The method of claim 10 wherein the step of using the determined value for the photosynthetic parameter to determine the physiological state of a plant comprises the step of comparing the determined value for the photosynthetic parameter to a reference value for the same photosynthetic parameter determined from spectral data obtained from one or more reference plants.

12. The method of claim 11 further comprising the step of observing a difference between the determined value for the photosynthetic parameter and the reference value for the photosynthetic parameter.

13. The method of claim 12 further comprising the step of correlating the difference between the determined value for the photosynthetic parameter and the reference value for the photosynthetic parameter with the presence of a physiological stress in the plant.

14. The method of claim 13 wherein:
(a) the photosynthetic parameter is electron transfer through photosystem I;
(b) the determined value for electron transfer through photosystem I is greater than the reference value for electron transfer through photosystem I; and
(c) the difference between the determined value for electron transfer through photosystem I and the reference value for electron transfer through photosystem I is correlated with the presence of heat stress in the plant.

15. The method of claim 13 wherein:
(a) the photosynthetic parameter is the electrochromic shift;
(b) the determined value for the electrochromic shift is greater than the reference value for the electrochromic shift; and
(c) the difference between the determined value for the electrochromic shift and the reference value for the electrochromic shift is correlated with the presence of heat stress in the plant.

16. The method of claim 13 wherein:
(a) the photosynthetic parameter is chlorophyll a fluorescence;
(b) the determined value for chlorophyll a fluorescence is greater than the reference value for chlorophyll a fluorescence; and
(c) the difference between the determined value for chlorophyll a fluorescence and the reference value for chlorophyll a fluorescence is correlated with the presence of heat stress in the plant.

17. The method of claim 13 wherein:
(a) the photosynthetic parameter is the ratio of the amplitudes of 820 nm absorbance and 525 nm absorbance;
(b) the determined value for said ratio is greater than the reference value for said ratio; and
(c) the difference between the determined value for said ratio and the reference value for said ratio is correlated with the presence of drought stress in the plant.

* * * * *

UNITED STATES PATENT AND TRADEMARK OFFICE
CERTIFICATE OF CORRECTION

PATENT NO. : 6,813,024 B2
DATED : November 2, 2004
INVENTOR(S) : D.M. Kramer et al.

It is certified that error appears in the above-identified patent and that said Letters Patent is hereby corrected as shown below:

<u>Title page,</u>
Item [56], References Cited, OTHER PUBLICATIONS, "Joliot, P., and A. Joliot," reference, "*Acta*765:210-218," should read -- *Acta*. 765:210-218, --
"Stacksteder, C.A., et al.," reference, "Stoichiom-
etry" should break -- Stoichio-
metry --; "is" should read -- Is --; and
"97926):14283-14288," should read -- 97(26):14283-14288, --.

<u>Column 1,</u>
Line 50, "i.e." should read -- (i.e., --

<u>Column 2,</u>
Line 36, "Thus" should read -- Thus, --

<u>Column 3,</u>
Line 4, "Thus" should read -- Thus, --
Line 50, "for example" should read -- for example, --

<u>Column 4,</u>
Line 7, "(2) is configured" should read -- (2) configured --
Lines 17 and 31, "(2) that is configured" should read -- (2) configured --
Line 49, "population of plants." should read -- in a population of plants. --

<u>Column 5,</u>
Line 58, "color" should read -- colored --

<u>Column 6,</u>
Line 61, "LEF–Linear" should read -- LEF–linear --

<u>Column 8,</u>
Line 54, "542 are" should read -- 542 is --

<u>Column 9,</u>
Line 21, "include" should read -- including --
Line 66, "FIG. 6, shows" should read -- FIG. 6 shows --

<u>Column 10,</u>
Line 5, "$v^2$" should read -- $v_2$ --

UNITED STATES PATENT AND TRADEMARK OFFICE
CERTIFICATE OF CORRECTION

PATENT NO. : 6,813,024 B2
DATED : November 2, 2004
INVENTOR(S) : D.M. Kramer et al.

It is certified that error appears in the above-identified patent and that said Letters Patent is hereby corrected as shown below:

Column 11,
Line 19, "(i.e." should read -- (i.e., --
Line 42, "processes," should read -- processes; --
Lines 50 and 58, "$b_{6f}$ complex" should read -- $b_6f$ complex --

Column 13,
Line 14, "Typically" should read -- Typically, --
Line 51, "plant; a decrease" should read -- plant; and a decrease --

Column 14,
Line 18, "516, was" should read -- 516 was --
Line 28, "Devices, )." should read -- Devices). --
Lines 30 and 33, "Middleboro" should read -- Middleboro, --
Line 55, "Palo Alto" should read -- Palo Alto, --
Line 61, "5030 and" should read -- 5030 or --

Column 15,
Line 16, "Measurements of steady-state absorbance change" should read
-- Measurements of Steady-State Absorbance Change --

Column 17,
Line 2, "shift on a cool" should read -- shift signals on a cool --

Column 18,
Line 15, "(1) alight" should read -- a light --

Signed and Sealed this

Thirty-first Day of May, 2005

JON W. DUDAS
*Director of the United States Patent and Trademark Office*